United States Patent [19]

Lazaridis et al.

[11] Patent Number: 4,990,610

[45] Date of Patent: Feb. 5, 1991

[54] METHOD FOR PREPARING HIGH POTENCY SUCRALFATE

[75] Inventors: Nick V. Lazaridis, Wilmington, N.C.; Moo K. Park, Fayetteville, N.Y.; Yousry Sayed, Wilmington, N.C.

[73] Assignee: Applied Analytical Industries, Inc., Wilmington, N.C.

[21] Appl. No.: 285,028

[22] Filed: Dec. 16, 1988

Related U.S. Application Data

[63] Continuation-in-part of Ser. No. 236,167, Aug. 25, 1988, abandoned.

[51] Int. Cl.$^5$ .................... C07H 11/00; C07H 13/12; A61K 31/715
[52] U.S. Cl. .................................................. 536/118
[58] Field of Search ........................... 536/118; 514/54

[56] References Cited

U.S. PATENT DOCUMENTS

| | | | |
|---|---|---|---|
| 3,271,388 | 9/1966 | Cammarata et al. | 536/107 |
| 3,432,489 | 3/1969 | Nitto et al. | 536/118 |
| 3,720,659 | 3/1973 | Guiseley et al. | 536/2 |

OTHER PUBLICATIONS

K. Ochi et al. Chem. Pharm. Bull 28(2) 638-641 (1980).
Nagashima et al. Arzneim Forsch 29: 1668 (1979).
The Merck Index, Tenth Edition No. 8755.
Chemical Abstracts No. 97: 198513p Maruko Pharmaceutical Co. Jpn. Kokai 82/67,595.
Chemical Abstracts vol. 104, Abstract No. 110116r, Montoro et al. Span. ES 519,512.
Chemical Abstracts Vol. 95, Abstract No. 187600x Maruko Pharmaceutical Jpn. Kokai 81/77,294.

*Primary Examiner*—Johnnie R. Brown
*Assistant Examiner*—Gary L. Kunz

[57] ABSTRACT

Sucralfate is prepared in good yields and in newly useful form first by reacting sucrose with chlorosulfonic acid in 2-picoline. The amonium salt is then formed and reacted with aluminum chlorohydrate in specific sequence and alcoholic solvent. The two distinct products have unexpected pharmaceutical and physical characteristics. The oral liquid suspensions also must be critically formulated.

17 Claims, No Drawings

METHOD FOR PREPARING HIGH POTENCY SUCRALFATE

This application is a continuation-in-part of Ser. No. 236,167, filed Aug. 25, 1988, now abandoned.

This invention relates to an improved chemical method for preparing the anti-ulcer medication, sucralfate, reproducibly in high purity and good yield.

BACKGROUND OF THE INVENTION

Sucralfate is, chemically, sucrose octakis(hydrogen sulfate) aluminum complex. When ingested, the complex adheres to ulcer surfaces in the gastrointestinal track, thereby shielding the ulcerated site from further destructive action by the digestive content of the track. The usual dose is 1 gram of sucralfate four times per day.

U.S. Pat. No. 3,432,489 describes the general synthesis of various disaccharide polysulfates and, therefrom, their aluminum complexes together with their relative therapeutic utilities. The reference, more specifically, describes the reaction of sucrose with many sulfating agents including chlorosulfonic acid or sulfur trioxide-pyridine in various solvents including pyridine. The use of the ammonium salt of the sucrose polysulfate intermediate is not described here. The second stage of the prior art process involves the reaction of a sucrose polysulfate or its alkali metal salt with a source of aluminum ion at a pH range of from 3.5–5.5, especially preferred 4–4.5, see Column 2, lines 33–34.

The complex products described in this reference are reported to be impure. Note the wide range of analytical values at column 1, line 20 and line 54 of the U.S. Pat. No. 3,432,489. A report on the chemical and biological relationships of sucralfate, which work must utilize the purest samples of drug available, by R. Nagashima et al., Arzneim. Forsch. 29 1668 (1979) reveals a large percentage of impurities. Examination of the elemental analyses reported by Nagashima suggests sucralfate content in the 70% range.

Other chemical methods to prepare sucralfate are reported in the art. Maruko, Japanese Patent No. 57/67595 (1982), discloses the preparation of sucrose polysulfate ammonium salt by sulfonation of sucrose with chlorosulfonic acid in formamide and, then, treatment of this impure ammonium salt with activated aluminum hydroxide to produce impure sucrose polysulfate basic aluminum salt. Japanese Patent No. 58/208294 (1983), describes the preparation of sugar polysulfate potassium salts with certain basic polyaluminum chlorides. Spanish Patent No. 519512 (1984), discloses the preparation of sucrose polysulfate sodium salt by treatment of sucrose with chlorsulfonic acid in pyridine and sodium hydroxide. This same patent further describes the conversion of sucrose octasulfate sodium salt to sucrose octasulfate aluminum salt by treatment with aluminum chloride.

Some of the above processes involve steps which are tedious and time consuming. Furthermore, these processes have the defect of low yield and undetermined purity of product. For example, the process of Japanese Patent No. 57/67595 produces impure sucrose polysulfate ammonium salt and consequently, impure aluminum complex product. Often the prior art processes give sucralfate products which do not demonstrate proper physical characteristics for full biological activity.

SUMMARY OF THE INVENTION

The object of this invention is to describe a chemical method which will produce high purity sucralfate cheaply and predictably. Also certain new pharmaceutical applications of the sucralfate produced by this improved method have been discovered. Finally, a new structural variation of sucralfate has been found which depends on the method of synthesis.

DETAILED DESCRIPTION OF THE INVENTION

The improved process of this invention for preparing sucralfate uses a critical selection of reactants and reaction conditions as described hereafter.

The initial chemical step of this process is the reaction of a purified powdered sucrose quantity with a previously prepared solution of an eightfold quantity of chlorosulfonic acid and either pyridine, or preferably, 2-picoline. The temperature of the initial reaction can range from about 40°–50° C. The use of these reagents, especially 2-picoline, enables one to use a wider range of reaction temperatures in the first step of process. The time of reaction is up to 1–2 hours or until the reaction is substantially complete.

The use of 2-picoline as solvent reactant has unexpectedly been found to give good yields and purity of product compared with pyridine. We have also found that the use of the isomer, 3-picoline, gives lower yields and quality of product. 4-Picoline, 2,3-lutidine, 2,5-lutidine and 3,5-lutidine all fail in the reaction. The novel successful use of this one methylated pyridine solvent is an unexpected aspect of this improved process.

The reaction mixture of the sucrose octasulfate is then reacted with an excess of aqueous ammonia, usually in situ, to produce the ammonium salt which is easily isolated by treatment of the mixture with an alcohol such as methanol, ethanol or 2-propanol. The intermediate salt product is obtained in quantitative yield of 80–90% pure salt. One recrystallization from aqueous ethanol gives a product purity of 95–100%.

To the best of our information, the ammonium salt has not been used previously in this way. (See Maruko, loc. cit. above.) It was described as a laboratory curiosity, K. Ochi et al., Chem. Pharm. Bull. 28 (2) 638 (1980). The use of this salt makes the use of ion exchange resin purification unnecessary.

This aspect of the improved process also obviates the presence of lower sulfated sucroses such as the troublesome sucrose heptasulfate in the intermediate product.

The sucrose octasulfate ammonium salt at a concentration of 30% (w/v) in water is added dropwise at room temperature with vigorous stirring to an aqueous aluminum chlorohydrate (at least 8 mole-equivalents) ($Al_2(OH)_5Cl \cdot 2H_2O$) solution in ethanol. The molar ratio of sucrose octasulfate ammonium salt to aluminum chlorohydrate is preferably about 1:8. The pH of this reaction is between 4.1 and 4.2 and may occasionally require adjustment to remove any excess chloride if present. Generally, the pH does not need control. The separated reaction product is isolated by centrifugation and washed with copious amounts of water to remove excess reagents. The sequence of reaction is important here, to give a high potency sucralfate product which may be formulated directly to prepare oral suspension compositions or may be dried to prepare solid oral dosage units.

The second step process illustrated above may be varied somewhat as will be apparent to those skilled in the art. Certain features are critical to preparing good product. First, the sequence of adding the sucrose octasulfate salt to a solution of the aluminum salt is important. As the literature suggests, the reaction is usually carried out in reverse and no indication is believed present in the art to suggest that the sequence of reaction should be reversed and is critical. Secondly, the reaction solvent should be one of the common alcoholic solvents such as methanol, isopropanol, ethylene glycol, and, especially, ethanol. Some water may be present. The prior art teaches running the reaction in water alone. The mole ratio should also be roughly stoichiometric, 1:8, but a small excess of the aluminum salt may be used.

The reaction is allowed to react until complete at room temperature. No particular advantage is apparent for varying time or temperature.

Commercial lots of sucralfate in the art must contain the active ingredient in the range of 72.2-91.3% calculated on the dried basis, (In process revision, Pharmacopeial Forum, page 4081, July-August, 1988). The high potency product of the invention will range from about 92-100% but usually and preferably 95-100%. This indicates not only a more active product but a more reliable product. Yields are also good, usually in the range of from about 95 to 100%.

The moist sucralfate product which is optionally isolated from the improved process described herein without the drying step has been found to be comprised of particles of size below about 30 microns, especially 5-10 microns, that is below those reported in the prior art. These sized particles have been found satisfactory to prepare directly liquid oral dosage unit forms such as suspensions or emulsions. These product forms are advantageous for oral product acceptance by the patient when medicament quantities are at large amounts, such as sucralfate at about 0.5 to 1 gram per dosage unit. The moist, sized product is mixed with formulating aids such as suspending agents or flavoring agents in quantities to give a dosage unit of reasonable concentration for ingestion by the patient suffering from ulcers. The moist product, prior to suspension, may alternatively be called a slurry or gel.

The moist product can be further air or heat dried as is common in the prior art. The dried product may be used as-is to produce the drug product in high potency form such as oral tablets or capsules. The product acts as does prior art sucralfate biologically and chemically.

We have also found unexpectedly that when the order of reaction is reversed from that described above, the alcoholic solvent reaction gives a product that has substantial physical and biological advantages to a "paste" product produced by acid treatment prior to biological activity at the wound site. The new product which is a product of this invention has inherent "sticky" or "paste" nature, without acid pretreatment. It is easy to handle and formulate. It has been found to be vastly superior in treating surface wounds than is the prior art sucralfate which has little activity or the high potency sucralfate described above which has weak wound activity. The new product has a structural difference when compared with sucralfate. The difference also gives it physical properties which make it easier to handle.

It will be further understood that the two chemical reactions of the overall improved method of this invention may be advantageously carried out without isolation of the intermediate ammonium salt of sucrose octasulfate. The improved process described herein has also been carried out successfully with other sugar reactants such as glucose, fructose, lactose, and maltose.

The following examples are embodiments of this invention and should not be construed as limiting its scope.

EXAMPLE 1

Chlorosulfonic acid (394.4 g, 3.39 mole) is slowly added to 2-picoline 1226 g, 13.2 mole) while the temperature is maintained at 40°-50° C. with vigorous stirring. Finely powdered sucrose (140 g, 0.41 mole) is added and the mixture is stirred for an additional one hour at 55°-65° C. Aqueous ammonia (14%) is added to bring pH to 7.5-8.0 while temperature is maintained below 30° C. Reagent alcohol (0.5 L) is added and stirring is continued until an oily product is solidified. The solid product is filtered, washed with reagent ethanol (400 ml) and dried under vacuum (0.5 mm Hg) at 45°-50° C. for twelve hours. This product is recrystallized from 1000 ml aqueous reagent ethanol (50/50) to produce 441 g of pure sucrose octasulfate ammonium salt.

Sucrose octasulfate sodium salt is optionally prepared by dissolving sucrose octasulfate ammonium salt (20 g) in water (100 ml). Aqueous sodium hydroxide (20%) is added to bring the pH to 8-9. Reagent ethanol is added to precipitate sucrose octasulfate sodium salt. This salt is filtered and dried as in the case of the ammonium salt.

EXAMPLE 2

Sucrose octasulfate ammonium salt (75 g) dissolved in distilled water (263 ml) is slowly added with vigorous stirring in 1350 ml of 50% aluminum chlorohydrate in alcohol at room temperature, over 4 to 6 hours. The mixture is allowed to stand for 12 hours.

The mixture is centrifuged, decanted and distilled water (500 ml) is added. The mixture is vigorously shaken and centrifuged. This process of washing is repeated four additional times. The mixture is filtered and the moist product is optionally dried at 55° C. for 12 hours to produce 125 g of sucrose octasulfate basic aluminum complex.

EXAMPLE 3

Sucrose octasulfate ammonium salt (200 g) dissolved in distilled water (600 ml) is slowly added over 4-6 hours with vigorous stirring to a solution of 576 g of 50% aluminum chlorohydrate in 2.3 liters of ethanol at room temperature. One liter of water is added to the mixture. Stirring is continued 1-3 hours. The mixture is allowed to stand overnight, then centrifuged. The wash was decanted and 2 liters of water is added. The mixture is vigorously shaken and centrifuged. The washing is repeated four times. The moist product is dried at 55° C. for 12 hours to produce 362 g of sucrose octasulfate basic aluminum complex. The following data reflect three runs of the same size carried out as above.

| Batch Number | Hydrous Purity by HPLC | Hydrous | | | | |
|---|---|---|---|---|---|---|
| | | % C | % H | % S | % Al | % $H_2O$ |
| 3-040 | 88.0 | 6.05 | 3.6 | 11.66 | 19.55 | 7.43 |
| 3-041 | 88.4 | 5.86 | 3.9 | 11.51 | 18.45 | 7.87 |
| 3-042 | 90.6 | 5.5 | 3.3 | 10.6 | 17.8 | 8.64 |

EXAMPLE 4

38 ml of a 50% solution of aluminum chlorohydrate, $(Al_2(OH)_5Cl.2H_2O)(0.120$ moles), is diluted with 38 ml of a 60% aqueous ethanol solution. This solution is added dropwise with stirring at ambient temperature over 1½ hours into a solution of sucrose octaammonium sulfate (0.015 moles in 750 ml of 60% aqueous ethanol).

The white powder precipitate is centrifuged and washed with copious amounts of 60% aqueous ethanol.

The wet material can be used as such or dried at 50° C. for 4 hours. The yield is approximately 100%.

The as-is purity of this material is 81.6% and the anhydrous purity is 97.6%. This material is the naturally "sticky" material mentioned above and is particularly useful for substitution in both the internal and particularly external pharmaceutical applications of sucralfate.

EXAMPLE 5

Oral suspensions containing high potency sucralfate, prepared as in Examples 2 and 3 above, at the range of 5% w/v–30% w/v have been prepared as described below. Sucralfate raw material in aqueous slurry was mixed with gum solution using a homo-mixer. Sweetening agent, saccharin or sucrose, and preservative, benzoic acid sodium salt, were mixed with continuous homogenization. Enough water was added to make the desired volume and homogenization was continued. Flavoring agent, such as peppermint, was added and the final mixture was homogenized.

|  | #1 | #2 | #3 | #4 | #5 |
|---|---|---|---|---|---|
| Sucralfate (as dry powder) | 5 | 10 | 20 | 30 | 30 |
| Hydroxypropyl-menthyl Cellulose E4M 4% w/w in water | 12.5 g | 12.5 g | 12.5 g | 16.7 g | 16.7 g |
| Sodium benzoate | 0.2 g | 0.2 g | 0.2 g | 0.2 g | 0.2 g |
| Saccharin | — | — | — | 0.2 g | — |
| Sucrose | 30 g | 30 g | 30 g | — | 13.3 g |
| Pepperming Flavor | 0.5 ml | 0.5 ml | 0.5 ml | 0.2 ml | 0.2 ml |
| Purified water q.s. to | 100 ml | 100 ml | 100 ml | 100 ml | 100 ml |

The suspension is packaged in proper containers for commercial sale.

For an adult, one teaspoon of suspension 3 (equivalent to 1 g sucralfate) is orally administered four times a day for the short-term treatment of duodenal ulcer.

In formulating the sucralfate oral suspensions, it was found that the palatability and physical stability of the suspensions depend on the presence of gum and amount of sucrose used. The chalky taste of the suspensions is accentuated by omitting the gum and by increasing the amount of sucrose over approximately 30% w/v.

The gum may be selected from alginates, gum arabic, gum tragacanth, guar gum, pectin, zanthan gum, methylcellulose, hydroxypropylmethyl cellulose, hydroxyethyl cellulose, and sodium carboxymethyl cellulose. It is used in sufficient quantities to impart acceptable viscosity to the suspension.

Sucrose alone in the suspension gives the suspension tendency to cake and make it difficult to resuspend. When sucrose is used in combination with gums, it is recommended that sucrose be used below 30% w/v.

What is claimed is:

1. The method for preparing sucralfate comprising:
   (a) reacting one equivalent of sucrose with at least 8 equivalents of chlorosulfonic acid which had been previously mixed and reacted with 2-picoline the latter at a temperature of about 40°–50° C. for from 1 to 2 hours;
   (b) adding aqueous ammonia at a temperature below 25° C. to bring the pH of the reaction mixture to about 7.5–8.0;
   (c) adding an excess of methanol, ethanol or 2-propanol to separate sucrose octasulfate ammonium salt;
   (d) purifying said separated salt by recrystallization from aqueous ethyl alcohol;
   (e) reacting said salt with aluminum chlorohydrate in an alcoholic solvent at a molar ratio of approximately 1:8;
   (f) allowing said reaction to go to completion at ambient temperature and the product to separate;
   (g) purifying said product by washing with water to produce said product in water moist form; and
   (h) drying said moist form to produce a powder product form.

2. The method of claim 1 in which said sucrose octasulfate ammonium salt is not isolated and purified but is used directly in step (e).

3. The method of preparing sucralfate comprising adding sucrose octasulfate ammonium salt to at least 8 equivalents of aluminum chlorohydrate in an alcoholic solvent at ambient temperature.

4. The method of claim 3 in which the alcoholic solvent is ethanol.

5. The method of claim 3 in which the alcoholic solvent is aqueous ethanol.

6. The method of claim 5 in which no excess over 8 equivalents of aluminum chlorohydrate is used.

7. The method of claim 3 in which the separated sucralfate is maintained in water moist form and further used directly to prepare liquid oral dosage unit pharmaceutical forms.

8. The method of claim 3 in which said sucralfate has, or is sized to have, a particle size below 30 microns.

9. The method of claim 8 in which said particle size is from 5–10 microns.

10. The method of claim 3 in which the separated sucralfate is purified by washing with water.

11. The method of claim 3 in which vigorous stirring is used during the reaction.

12. The method of claim 3 in which the addition is slowly over a period of from 1–3 hours at ambient temperature.

13. The method of claim 3 in which the sucralfate is separated and heat dried.

14. The method of claim 3 in which the product sucralfate is formulated into a liquid or solid oral dosage unit composition.

15. The method of claim 3 in which the product sucralfate is formulated into an oral suspension product form which has an aqueous base with a gum sufficient to impart greater than aqueous viscosity and a sweetening agent.

16. The method of claim 15 in which the sweetening agent is sucrose and the gum is hydroxypropylmethyl cellulose.

17. In the method of preparing sucrose octasulfate by reacting sucrose with at least 8 molar equivalents of chlorosulfonic acid, the improvement comprising the use of 2-picoline as reactant-solvent.

* * * * *